(12) United States Patent
Krivitski et al.

(10) Patent No.: US 7,275,447 B2
(45) Date of Patent: Oct. 2, 2007

(54) METHOD AND APPARATUS TO DETERMINE AN INITIAL FLOW RATE IN A CONDUIT

(75) Inventors: Nikolai M. Krivitski, Ithaca, NY (US); Cornelis J. Drost, Ithaca, NY (US)

(73) Assignee: Transonic Systems, Inc., Ithaca, NY (US)

( * ) Notice: Subject to any disclaimer, the term of this patent is extended or adjusted under 35 U.S.C. 154(b) by 0 days.

(21) Appl. No.: 11/674,448

(22) Filed: Feb. 13, 2007

(65) Prior Publication Data

US 2007/0137296 A1 Jun. 21, 2007

Related U.S. Application Data

(60) Division of application No. 11/456,751, filed on Jul. 11, 2006, now Pat. No. 7,210,359, and a continuation of application No. 11/084,271, filed on Mar. 18, 2005, now Pat. No. 7,121,150, and a continuation of application No. 09/419,849, filed on Oct. 19, 1999, now Pat. No. 6,868,739.

(51) Int. Cl.
*G01F 1/00* (2006.01)
*A61B 5/02* (2006.01)

(52) U.S. Cl. ............ 73/861.05; 73/861; 600/506; 600/507

(58) Field of Classification Search .............. None
See application file for complete search history.

(56) References Cited

U.S. PATENT DOCUMENTS 5,594,179 A * 1/1997 Marsh ............... 73/861.07

5,900,726 A    5/1999 Brugger et al.
6,125,934 A * 10/2000 Lenn et al. ............ 73/152.29
6,167,765 B1    1/2001 Weitzel

OTHER PUBLICATIONS

J. Sands, et al.;Transonic Hemodialysis Monitor; Difference Between Delivered and Prescribed Blood Flow (QB) in Hemodialysis; ASAIO '96.

Greenwood, R.N., Aldridge, C. and Cattell, W.R., Serial Blood Water Estimations And In-Line Blood Viscometry: The Continuous Measurement Of Blood Volume During Dialysis Procedures; *Clinical Sciences*, (1984) 66. p. 575-583.

Kaye, M., Lemaitre, P. and O'Regan, S., A New Technique For Measuring Blood Flow in Polytetrafluorethylene Grafts For Hemodialysis.

O'Regan, S., Lemaitre, P. and Kaye, M., Hemodynamic Studies In Patients With Expanded Polytetrafluoreothylene (PTFE) Forearm Grafts. pp. 96-100.

Paulo Rocha, MD, Jean-Claude Kahn, M.D. Gerard Dongradi, M.D., Bernard Baron, M.D. and Jean-Pierre Fendler, M.D., Arteriovenous Shunt Measured by Bolus Dye Dilution: Reproducibility and Comparison Between Two Injection Sites; Catheterization and Cardiovascular Diagnosis 11:473-481 (1985).

(Continued)

*Primary Examiner*—Harshad Patel
(74) *Attorney, Agent, or Firm*—Brian B. Shaw; Stephan B. Salai; Harter Secrest & Emery LLP

(57) ABSTRACT

A method and apparatus for determining an initial flow rate in a conduit is disclosed. A known change is made to the flow to be measured, resulting changes (or values corresponding to these changes), or relative changes in the flow to be measured are monitored and the initial flow in the conduit is calculated from the value of the known change and monitored changes. Devices to practice the method include catheters having one or two sensors and one or two sites for introducing the volume change.

10 Claims, 11 Drawing Sheets

OTHER PUBLICATIONS

Carol L. Miranda, Increasing AV Fistulas for Hemodialysis Access, Dialysis: Access/Methods of Hemodialysis, #205, JASN, Sep. 1995, vol. 6, No. 3.

Daniel Schneditz and Thomas Kanner, A Sound Speed Sensor For The Measurement Of Total Protein Concentration. J. Acount Soc. Am. 86 (6), Dec. 1989 p. 2073-2080.

T. Buur and E.J. Will, Maemodialysis Recirculation Measured Using A Femoral Artery Sample, Nephrol Dial Transplant (1994) 9: p. 395-398.

T.A. Depner and N.M. Krivitski, Influence of Access Blood Flow on Systemic Blood Flow in Hemodialysis Patients, JASN vol. 8, pp. 155A, 1997 (HD23A).

Thomas A. Depner and Nikolai M. Krivitski, Clinical Measurement of Blood Flow in Hemodialysis Access Fistulae and Grafts by Ultrasound Dilution, ASAIO; Jul.-Sep. 1995, vol. 41, No. 3, Lippincott-Raven Publishers, U.S.A.. Journal, Jul.-Sep. 1995, Lippincott-Raven Publishers, vol. 41, No. 3.

V.A Del Grosso and C.W. Mader, Speed of Sound in Sea-Water Samples.

L. Forsberg. U. Tylen, T. Olin and E. Lindstedt, Quantitative Flow Estimations Of Arteriovenous Fistulas With Dopper And Dye-Dilution Techniques, p. 465-468.

S. Gottlieb, E. Garcia, S.B. Cold, and B.A. Vanderwerf, Radiotracer Method For Nonsurgical Measurement Of Blood Flow In Bovine Graft Arteriovenous Fistulas, Proc. Dialysis Transplant Forum, 1976, p. 107108.

James F. Greenleaf, Ph.D, Tissue Characterization With UltraSound, vol. II, Results and Applications, CRC Press, Inc., Boca Raton, FL.

Daniel Schneditz, et al., Cardiopulmonary Recirculation in Dialysis, ASAIO Journal 1992, p. M-194-M-196.

E.L. Bradley, et al., The velocity of ultrasound in Human Blood Under Varying Physiologic parameters.

Guyton, Textbook of Medical Physiology, p. 287-288.

Nikolai M. Krivitski and Thomas A Depner, Development of a Method for Measuring Hemodialysis Access Flow: From Idea to Robust Technology; Research in Dialysis, p. 124-130.

Nikolai M. Krivitski and Thomas A Depner, Influencer of Access Bloow Flow on Systemic Blood Flow in Hemodialysis Patients; Dialysis; Methods of Hemodialysis and Vascular Acces, p. 155AS.

M. Germain, Correlation of Weekly Access Blood Flow Rate and Access Stenosis and Clotting; Dialysis: Access/Methods of Hemodialysis; p. 1407.

Nikolai M. Krivitski and Thomas A Depner, Access Flow Measured from Recirculation of Urea During Hemodialysis with Reversed Blood Lines; Dialysis: Access/Methods of Hemodialysis, #198.

Leif Ekelund, Jan Gothlin and Tord Olin, Arteriovenous Fistulae in Rabbit Kidney Studies by Dye-Dilution Technique and by Angiography; Scand J. Uron Nephrol 6: 84-90, 1972.

Jan Gothlin Eric Linstedt and Tord Olin, A Dye-Dilution Method for the Determination of Blood Flow in Cimino-Brescia Arteriovenous Fistulae, Copyright 1997 by the Williams & Williams Company.

Robert L. Hester, et al.; Non-Invasive Determination of Recirculation in the Patient on Dialysis; ASAIO Journal 1992, p. M190-193.

Nikolai M. Krivitski, Blood Flow Measurement in PTFE Hemodialysis Grafts (HG) By Ultrasound Velocity Dilution (in Vitro Validation); Dialysis: Access/Methods of Hemodialysis.

C. Aldridge, et al., Instrument Design for the Bedside Assessment of Arteriovenous Fistulae in Haemodialysis Patients; Proc EDTNA-ERCA (1985) vol. 14 p. 255-260.

N.M. Krivitski, et al.; Vascular Access Flow Changes with Normal or Reversed Hemodialysis Blood Flow; ASAIO, Jan.-Feb. 1996, p. 80.

Daniel Schneditz, et al.; On-Line Measurement of Blood Water Concentration in the ExtrCorporeal Circulation of Hemodialysis Patients; Annual International Conference of the IEEE Engineering in Medicine and Biology Society, vol. 13, No. 4, 1991.

I.D. Daniels, G.M. Berlyne, R.H. Barth, Blood Flow Rate and Access Recirculation in Hemodialysis; The International Journal of Artificial Organs, vol. 15, No. 8, 1992, pp. 270-474.

P. Chanmey, et al., Modelling Cardiopulmonary and Fistula Recirculation.

Gunnar Lindgardh and Bo Lundstrom, Renal Bloow Flow in Man Studies with Dye Dilution Method; Scandinavian Journal of Urology and Nephrology, vol. 6, No. 1, 1972, p. 54-62.

Shahbudin H. Rahimtoola, et al., Calculation of Cardiac Output from Indicator-Dilution Curves in the Presence of Mitral Regurgitation; *Circulation*, American Heart Association, vol. XXXI, No. 4, 1965.

C. Norryd, et al.; Superior Mesenteric Blood Flow in Man Studies with a Dye-Dilution Technique; Aeta Chir Scand 141: 109-118, 1974.

H. Dencker, et al., Portal Circulation In Humans Studies by a Dye-Dilution Technique; European Surgical Research, vol. 4, No. 2 (pp. 81-152), 1972.

L. Jorfeldt and J. Wahren, Leg Blood flow During Exercise in Man, *Clinical Science*, 1971, 41, pp. 459-473.

R.N. Greenwood, et al., Assessment of Arteriovenous Fistulae From Pressure And Thermal Dilution Studies: Clinical Experience In Forearm Fistulae, *Clinical Nephrology*, Vo. 23, No. 4-1985 (pp. 189-197).

R. Andres, Measurement of Blood Flow and Volume in the Forearm of Man; With Notes on the Theory of Indicator-Dilution and on Production of Turbulence, Hemolysis and Vasodilation by Intra-Vascular Injection; *The Journal of Clinical Investigation*, Vol. XXXIII, 1954, pp. 482-504.

Jan Gothlin, Tord Olin, Dye Dilution Technique with Nephroanglography for the Determination of Renal Blood Flow and Related Parameters; *Acta Radiologica*, vol. 14, Fasc. 1, Jan. 1973.

J. Wahren and L. Jorfeldt, Determination of Leg Blood Flow During Exercise in Man: An indicator-Dilution Technique based on Femoral Venous Dye Infusion; *Critical Science and Molecular Medicine* (1973), 45, 135-146.

N. Krivitski, et al.; Saline release method to measure access flow by ultrasound dilution during hemodialysis; Dialysis: Methods of Hemodialysis and Vascular Access, p. 164A.

Michael Simonsen, Ph.D., Innovation pace remains rapid in interventional cardiology, American Health Consultants®, vol. 4 No. 5.

Michael Simonsen, Ph.D., Interventional radiology market is diverse and growing rapidly, American Health Consultants®, vol. 5 No. 6.

A. Fronek, M.D., V. Ganz, M.D., Measurement of Flow in Single Blood Vessels Including Cardiac Output by Local Thermodilution, Circulation Research, vol. VIII, Jan. 1960.

Kenneth F. Hosel, Thermal-Dilution Technics, Circulation Research, vol. 1, Mar. 1962.

James L. Linzell, PH.D, Measurement of Venous Flow by Continuous Thermodilution and its Application to Measurement of Mammary Blood Flow in the Goat, Circulation Research, vol. XVIII, Jun. 1966.

* cited by examiner

ΔV2

METHOD AND APPARATUS TO DETERMINE AN INITIAL FLOW RATE IN A CONDUIT

CROSS-REFERENCE TO RELATED APPLICATIONS

This application is a division of U.S. patent application Ser. No. 11/456,751, filed Jul. 11, 2006, now U.S. Pat. No. 7,210,359 entitled Method and Apparatus to Determine an Initial Flow Rate an a Conduit, which is a continuation of U.S. patent application Ser. No. 11/084,271, filed Mar. 18, 2005, now U.S. Pat. No. 7,121,150, issued Oct. 17, 2006, entitled Method and Apparatus to Determine an Initial Flow Rate in a Conduit, which is a continuation of U.S. patent application Ser. No. 09/419,849, filed Oct. 19, 1999, now U.S. Pat. No. 6,868,739 issued on Mar. 22, 2005, entitled Method and Apparatus to Measure Blood Flow by an Introduced Volume Change, which applications are hereby incorporated by reference.

BACKGROUND OF THE INVENTION

1. Field of the Invention

The present invention relates to flow measurements, and more particularly to blood flow measurements in biomedical diagnostic and research applications, wherein a flow rate is determined from sensed relative changes in the flow resulting from a known introduced volume change in the flow.

2. Description of Related Art

Commonly used methods to measure blood flow in biomedical diagnostic and research applications include indicator dilution, transit-time ultrasound, Doppler ultrasound, electromagnetic, nuclear magnetic resonance and x-ray fluoroscopy principles.

The measurement of blood flow is particularly important during vascular reconstructive procedures. In such procedures, the interventional cardiologist/radiologist attempts to restore blood flow in a diseased vessel, so measurement of the efficacy of the procedure constitutes important feedback. While prior methods have practical uses during specific medical studies and protocols, no method has been developed that has found widespread use during vascular reconstructive procedures.

A well-accepted blood flow measurement technique employing indwelling catheters is the indicator dilution method, often named Stewart-Hamilton methods after the inventors who pioneered this family of methods in the late 19th and early 20th century. In this method, an additional element is introduced into or extracted from the blood stream, or a blood property is changed (the "indicator"). A calibrated sensor placed downstream from the point of indicator introduction measures the absolute concentration of the indicator. Via well known equations one can then derive the volume flow at the point of mixing of the indicator with the blood flow. These methods are widely used for cardiac output measurement using pulmonary artery catheters. The method has not found use during interventional procedures likely because it requires pre-calibrated concentration sensors. The calibration of commonly used sensors such as thermal or electrical is affected by changes in vessel diameter.

Therefore, the need exists for determining flow rate in real time during vascular interventional procedures where catheters may be introduced into the patient. The need also exists for determining flow rate during a medical procedure so that the efficacy of the procedure can be determined, thereby reducing complications and subsequent interventions. The need also exists for determining flow in a broad spectrum of applications, without requiring extensive modifications of surgical procedure or retraining of surgical staff.

BRIEF SUMMARY OF THE INVENTION

The present invention provides a new class of flow measurement where an initial flow, the flow to be measured, is purposely altered. Without limiting the scope of this method, we will refer to this method hereby as the "volume change method".

The present family of volume change methods to measure an initial flow rate implement the following steps: introducing (i.e., injecting or withdrawing) a known volume of fluid over a known time (or measured time), that is, introducing a known flow rate to the initial flow rate such that the "introduced volume change" will produce one or more "resulting changes" in the flow to be measured; monitoring, directly or indirectly, values which correspond to the resulting changes; and determining the initial flow rate from the induced volume change and the monitored values.

The present invention further provides for the determination of flows during the introduced volume change. The invention also provides for calibration of flow sensors and sensor methods. The volume change method of measuring flow has a further usage as a means to calibrate the volume flow sensitivity of flow sensors, pressure sensors and dilution sensors. The present invention may also employ blood velocity measurement, pressure measurement and indicator dilution measurement techniques.

The present invention also includes an apparatus for determining the flow rate in a conduit. The apparatus includes a sensor for sensing a change resulting from the introduction of a known flow rate and a controller for determining the initial flow rate in the conduit corresponding to the sensed change and the introduced known flow rate.

In a further application of the invention, a catheter is introduced into the cardiovascular circuit of a patient, and specifically into the vessel in which the flow rate is to be determined. A metered volume change is made to the initial flow in the vessel through the catheter. Resulting changes in the vessel flow (or corresponding values) are monitored and the initial flow rate in the vessel is determined. The resulting changes may be monitored by sensors located inside the conduit, outside the vessel, on the skin or even remote from the patient.

The volume change method employs, in some of its embodiments, changes in indicator concentration as a means to assess relative changes in local flow in a conduit. These methods bear some similarity to the conventional indicator dilution family of methods, often called Stewart-Hamilton and Fick principle methods. Indicator dilution methods use indicator concentration as the primary means to assess blood flow, according to a simple principle: if one introduces a known amount of indicator in a flow and monitors downstream the resulting absolute concentration of that indicator, one can deduce the volume rate of flow. Indicators are used differently in the volume change method. In conventional indicator dilution methods the volume of the introduced indicator must be known and the concentration curve is recorded and analyzed in adequate absolute units, such as "rems per ml/min" for a radioisotope indicator, or "calorie change per ml/min" for thermal dilution. No such absolute calibration is needed for the present volume change method: in the indicator embodiments of the volume change method, only values proportional to concentration changes are required to calculate the flow in the conduit. Neither the amount of the introduced indicator nor the actual concentration changes need to be determined.

BRIEF DESCRIPTION OF THE SEVERAL VIEWS OF THE DRAWING(S)

DETAILED DESCRIPTION OF THE INVENTION

Figure 1:
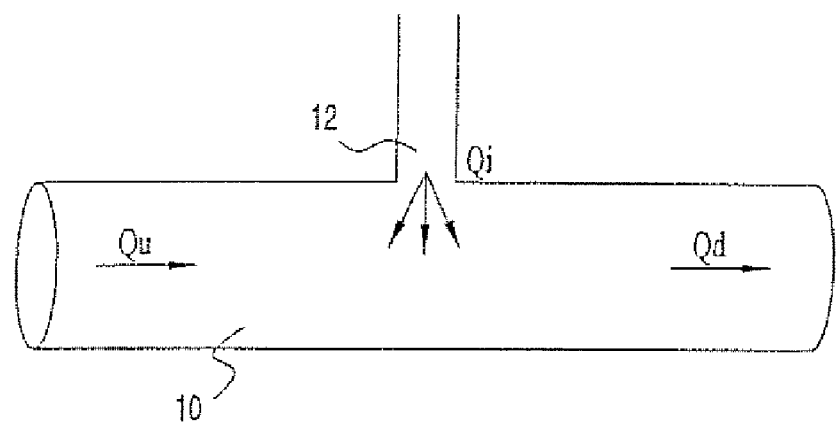
FIG. 1 is a schematic showing flows in a conduit with a side branch for introducing a volume change.
Figure 2:
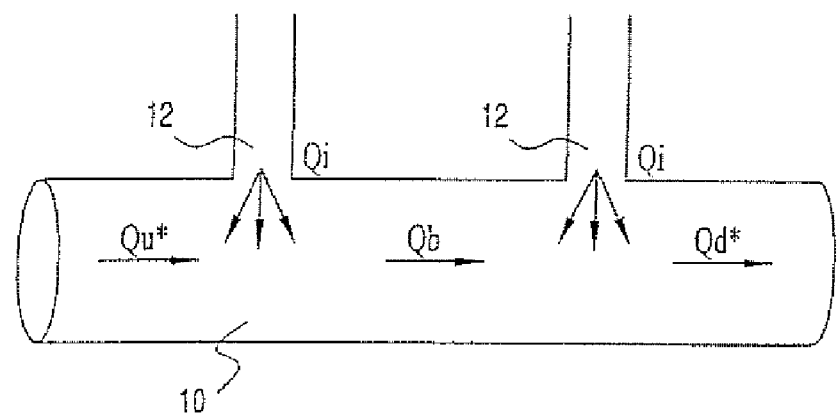
FIG. 2 is a schematic showing flows for two spaced apart injections functioning as volume changes.

The present invention provides for the determination of a volumetric flow rate ("flow rate") in a conduit by the volume change method. The conduit may be any of a variety of liquid conducting members including arteries, veins, heart chambers, shunts, vessels, tubes and lumens. Thus, the term conduit encompasses each of these as well as any other flow-conducting element. The volumetric flow rate is a measure of the volume of liquid passing a cross-sectional area of the conduit per unit time, and may be expressed in units such as milliliters per min (ml/min) or liters per minute (l/min). A liquid flow having a flow rate also has a flow velocity, the distance traveled in a given time, such as millimeters per second (mm/s). Thus, for liquid flowing in a conduit, there will be a flow rate (volumetric flow rate) having a flow velocity.

The present invention includes the volume change measurement method which encompasses the following steps: (i) introducing a known volume change to the flow to be measured; (ii) monitoring the relative change(s) (or values corresponding to these) in the flow to be measured which result from the introduced volume change; and (iii) calculating the initial flow in the conduit (i.e., the flow existing in the conduit before the introduced volume change) from the known volume change and the relative change(s).

A volume change may consist of a circulating volume change or it may be a discrete volume change such as an injection or withdrawal of a volume of liquid. The circulating volume change includes the simultaneous withdrawal of liquid (such as blood) from the conduit and the return delivery of the liquid (or a different liquid) back into the conduit, usually with a pump or other extracorporeal system. The returned liquid may have been modified via a secondary system such as a blood treatment device. The withdrawal and return delivery may be performed in different vessels of the cardiovascular circuit. In contrast, the discrete volume changes do not include simultaneous withdrawal and return of a liquid. That is, if there is a withdrawal or injection of liquid, the fluid flow during this volume change is either into or out of the system, without a corresponding simultaneous flow in the opposite direction. A withdrawal and a subsequent injection to the initial flow is encompassed by the discrete volume change as there is no circulating (simultaneous withdrawing and injecting).

It is understood that the term "volume change" includes, but is not limited to any and all methods that induce a change in the volumetric flow rate in the conduit in which flow is to be measured, including but not limited to: the introduction of a known bolus of liquid into the liquid stream in the conduit; the withdrawal of a known bolus from the flow in the conduit; the simultaneous or successive introduction and/or withdrawal of a plurality of boluses; the introduction or the withdrawal of a metered flow rate; the simultaneous or successive introduction and/or withdrawal of several metered flow rates; the combination of a metered flow rate change and a bolus injection or withdrawal; the step-wise alteration of the diameter of a section of a catheter (or other variable cross section device) inserted into the flow stream in the conduit, the introduction or withdrawal of a solid volume into/out of the flow stream in the conduit, and the alteration of the cross sectional volume of the conduit over a certain conduit length by altering its cross sectional geometry. All of these introduce a metered change (known flow rate) to the flow to be measured in the conduit. This metered change in flow, independent of how the change is induced, constitutes the "volume change." The volume change is a known volume over a known time. That is, a known, (measured or measurable) change is introduced to the initial flow whose flow rate is to be determined.

In the general case, the introduced volume change will effect changes to the flow in the conduit both upstream and downstream from the site of the introduced volume change. However, it is understood, the changes resulting from the volume change may include changes to the characteristics, properties or parameters of the liquid ("liquid characteristic") as well as the characteristics, properties or parameters of the flow ("flow characteristic"). This includes changes that are proportional or correspond to the liquid or the flow. For example, if the liquid characteristics are sensed, the optical, electrical, thermal or material aspects may be sensed. Specifically, the electrical conductivity, optical transmissivity, or temperature, velocity of sound or Doppler frequency. The flow characteristics include velocity, rate or pressure of the flow.

To calculate the initial flow, one would therefore monitor changes in flow in the conduit, both upstream and downstream from the point of the induced volume change in the flow. This can be implemented in two configurations: one introduced volume change and two sensors, or two introduced volume changes and one sensor.

In the first configuration, one sensor monitors changes to the conduit flow downstream of the introduced volume change, the other sensor monitors changes upstream of the introduced volume change. In the second configuration one could alter the location where the volume change is introduced: one volume change is induced upstream, the other volume change is induced downstream of a sensor located at a fixed position. In an alternative embodiment of the second configuration, the properties of a single sensor could be changed such that one sensing location would be upstream, the other sensing location would be downstream from the fixed location where the volume change is introduced.

At certain positions within a flow geometry, the volume change will only (or predominately) affect the conduit flow downstream or upstream from the point where the volume change is introduced. For example, a volume change introduced in a conduit connected to a fixed-output pump will only affect flow downstream from the point of change. A change introduced at the base of the pulmonary artery will primarily change pulmonary flow and not the output of the right ventricle. In such cases, the volume change method can be implemented by only measuring relative changes in flow downstream from the point of introduced volume change.

In other instances, the induced volume change will primarily alter conduit flow upstream from the point where the volume change is introduced. For example, the microvasculature of a capillary network represents a relatively large resistance to blood flow, while a healthy arterial bed feeding these capillaries may represent a relatively low resistance to blood flow. At such a location, most of the introduced volume change would flow retrograde in the introduced artery, and it will suffice to measure relative changes in flow only upstream from the point of change introduction. The venous return path within the cardiovascular geometry, similarly, offers areas where a measurement simplification can be made. The full venous return system operates at a low liquid pressure. Its capacity to accept an introduced liquid injection is therefore great: the veins will just extend a bit to accept the introduced volume. However, the peripheral veins also incorporate one-way valves: retrograde flow is automatically blocked. Therefore, if a volume change of sufficient magnitude is introduced in such a vein, the upstream flow will automatically drop to zero. This removes the need to implement an upstream sensor, and flow in the vessel can be calculated from just a downstream recording of the change of flow, the volume change (the volume/unit time), and the flow configuration assumptions.

It is understood that the sensing of changes resulting from a volume introduction includes, but is not limited to any and all methods may register such a change: the direct measurement such a change, the indirect recording of a secondary affect caused by such a change, or the recording of an effect which corresponds to such a secondary affect. Without limiting the scope of the disclosed invention, the preferred embodiments focus on three such change sensing methods: sensing of changes in blood transport (flow or flow velocity), sensing changed blood chemical or physical properties (indicator dilution) and sensing changes in pressure.

The volume change method of measuring flow has a further usage as a means to calibrate the volume flow sensitivity of flow sensors, pressure sensors and dilution sensors. After the steps of introducing a change in flow and sensing the relative changes in flow which result from the volume change, the calculation of the actual volume rate of flow in the conduit is synonymous to calculating the sensor's volume flow sensitivity. Thus, the velocity-to-volume flow conversion factor of a flow velocity sensor (such as an extracorporeal Doppler sensor, perivascular or intravascular transit time sensor or an implanted electromagnetic sensor) and uncalibrated indicator concentration sensor can be readily determined by the volume change method. The sensor can be employed from then on (so long as its flow sensing geometry is unaltered) to report volume flow directly without the added steps of the volume change method.

Theory

Figure 3:
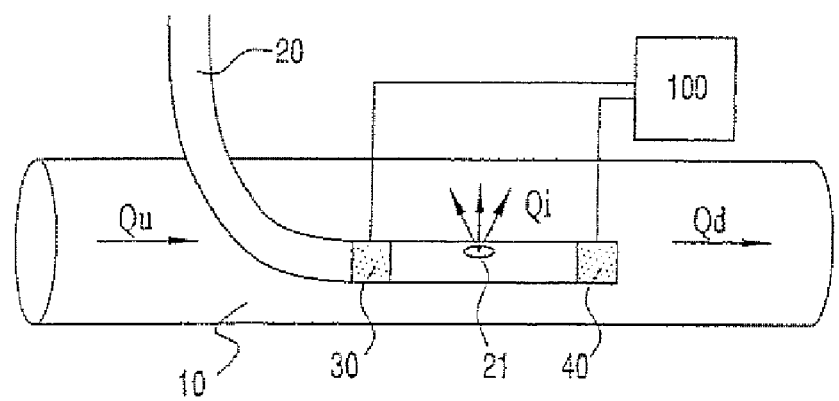
FIG. 3 is a representative view of a conduit having a catheter for introducing a volume change and monitoring a resulting upstream change and a resulting downstream change.

Referring to FIG. 1, a flow in a conduit 10 has an input (upstream) flow Qu and outgoing (downstream) flow Qd. The conduit 10 can be an artery, vein, artificial vessel or any other channel of flow. Via a side branch 12, a temporary flow Qi (the volume change) can enter or leave the flow conduit 10. In a typical clinical application as disclosed in this invention, as shown in FIG. 3, a catheter 20 is located in the conduit 10. The catheter 20 includes a port 21 for introducing the volume change, the port being intermediate an upstream sensor 30 and a downstream sensor 40. In a typical clinical application, Qi may result from the volume change passing through the catheter port 21 between the points where Qu and Qd are monitored (FIG. 3). Assuming a steady-state condition, where the volume of the conduit 10 does not change during the measurement interval, the law of conservation of mass is applied to define the relationships between these flows.

Before and after the volume change (injection/withdrawal) period, flow into the conduit Qu equals flow out of the conduit Qd and equals initial flow Q:

$$Q=Qu=Qd \qquad \text{(Eq. 1)}$$

During the injection period (suffix i) the following flow equation describes the conservation of mass (see FIG. 1):

$$Qui+Qi=Qdi \qquad \text{(Eq. 2)}$$

Subtracting Eq. (1) from Eq. (2) and dividing the resulting equation by Q (=Qu=Qd) yields:

$$\frac{Qui - Qu}{Qu} + \frac{Qi}{Q} = \frac{Qdi - Qd}{Qd} \qquad \text{(Eq. 3)}$$

Setting Qui−Qu=ΔQu and Qdi−Qd=ΔQd. ΔQu and ΔQd can be positive or negative: a positive value indicates an increase in flow; a negative value indicates a decrease in flow. Rearranging the terms yields an expression for the initial flow in the conduit:

$$Q = \frac{Qi}{\left(\frac{\Delta Qd}{Qd} - \frac{\Delta Qu}{Qu}\right)} \qquad \text{(Eq. 4)}$$

This equation is central to the present volume change method. It states that the undisturbed flow in the conduit 10 (vessel) before/after the introduced volume change is calculated from the introduced volume change (here expressed by its flow rate Qi), and the relative measurement of changes in flow upstream and downstream from the volume change introduction site. For simplicity, the equation can be rewritten as:

$$Q = \frac{Qi}{(Cd - Cu)} \qquad \text{(Eq. 5)}$$

where: Cd=ΔQd/Qd, is the relative change in a flow-corresponding parameter downstream from the point where flow is changed, Cu=ΔQu/Qu, is the relative change in a flow-corresponding parameter upstream from the point where flow is changed. In a typical implementation of the volume change method where a bolus of liquid is injected, the downstream flow increases (positive Cd) and the upstream flow decreases (negative Cu). So, the (Cd−Cu) factor is the sum of two positive numbers.

The ratio between Cd and Cu reveals where the resistance to changes in flow exists. If the volume change site (location) is just downstream from a fixed-output flow source such as the heart, Cu will be near zero, and the flow Qh in such a vessel can be measured with a single sensor:

$$Qh = \frac{Qi}{Cd} \qquad \text{(Eq. 6)}$$

In other instances the downstream flow may be much more resistant to change that the upstream flow, meaning that Cd can be neglected in comparison to Cu. Such may be the case at a volume change location near the capillary part of the cardiovascular circulation. In that instance the flow Qc can be measured with a single sensor as:

$$Qc = \frac{Qi}{Cu} \qquad \text{(Eq. 7)}$$

A third opportunity for a single sensor measurement exists in the venous vasculature at locations where one-way valves stop or inhibit retrograde flow. If the introduced volume change consists of an injected flow which is larger than the flow before the injection, flow upstream from the injected volume change will drop to zero (Qui=0) during the volume change period. Applying the definitions used above, Cu=−1, and the flow value Qv that existed in the vein before the volume change was introduced equals:

$$Qv = \frac{Qi}{(Cd + 1)} \qquad \text{(Eq. 8)}$$

Returning to the general case described by Eq. 5, where a single introduced volume change is sensed by both an upstream sensor 30 and a downstream sensor 40, each sensor provides an output which corresponds to flow (FIG. 1), which provides a basis for further calculations. Before the volume change, the upstream sensor 30 reports measurement values Mu, the downstream sensor 40 reports a measurement values Md. Index i indicates the measurement values reported by these sensors during the introduced change:

$$Mu = \alpha Q \qquad \text{(Eq. 9)}$$

$$Md = \beta Q \qquad \text{(Eq. 10)}$$

$$Mui = \alpha Qui \qquad \text{(Eq. 11)}$$

$$Mdi = \beta Qdi \qquad \text{(Eq. 12)}$$

In these equations, α and β are the volume flow calibration factors for the upstream sensor and the downstream sensor, respectively. Combining Eq. 5 with Eqs. 9 through 12 yields values for these volume flow calibration factors:

$$\alpha = \frac{Mu}{Qi}(Cd - Cu) \qquad \text{(Eq. 13)}$$

$$\beta = \frac{Md}{Qi}(Cd - Cu) \qquad \text{(Eq. 14)}$$

Thus, the volume change method can be used to establish the volume flow calibration factors of the upstream sensor 30 and the downstream sensor 40.

By substituting these Eqs. 13 and 14 into Eqs. 11 and 12, the values for the flows at the sensor locations during the introduced volume change in flow, Qui and Qdi can be calculated:

$$Qui = \frac{Mui \cdot Qi}{Mu} \Big/ (Cd - Cu) \qquad \text{(Eq. 15a)}$$

$$Qdi = \frac{Mdi \cdot Qi}{Md} \Big/ (Cd - Cu) \qquad \text{(Eq. 15b)}$$

Figure 8:
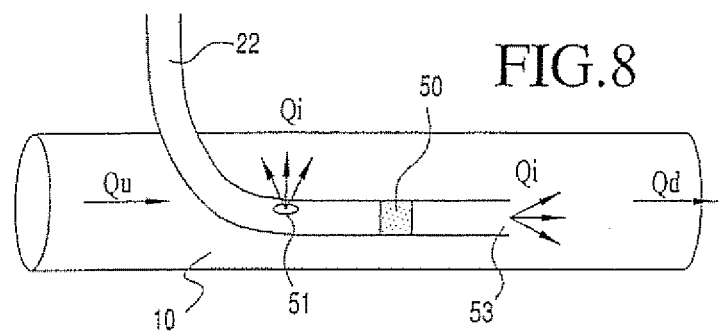
FIG. 8 is a representative view of a catheter in a conduit, the catheter having a single sensor intermediate a pair of volume change sites.

FIG. 8 depicts a one-sensor 50, two volume change site (upstream site 51 and downstream site 53) (injection/withdrawal ports) implementation of the volume change method. FIG. 8 depicts how this configuration may be implemented in practice, using a double lumen catheter 22 with one flow parameter sensor 50. An index * is used for the flow definitions in this configuration. Before the introduction of any volume change, the following flows in all sections of the conduit 10 are equal to each other:

$$Q = Qu^* = Qb^* = Qd^* \qquad \text{(Eq. 16)}$$

where Q*, Qu*, Qb* and Qd* are values of the initial blood flow, and blood flows upstream of, between, and downstream of the two volume alteration sites, respectively.

FIG. 8 depicts how this configuration may be implemented in practice, using a single catheter. The catheter 20 of FIG. 8 includes the upstream port 51, a downstream port 53 and an intermediate sensor 50. Volume changes can be introduced by first introducing an upstream volume change into the upstream port 51 in the catheter 22, then introducing a downstream volume change into the downstream port 53 of the catheter. For simplicity, the volume change in the upstream port 51 is selected equal to the volume change into the downstream port 53 and =Qi. Flow measurements made during the injection will again be indicated by the suffix i. There are now two different kinds of measurements on the Qb sensor 50: one where the sensor indicates the downstream flow changes resulting from the first injection (=Qbdi) and one where the sensor indicates upstream flow changes resulting from the second injection (Qbui). The conservation of mass principle yields the following equations for the two injections:

$$Qui^* + Qi = Qbdi^* \quad \text{(Eq. 17a)}$$

$$Qbui^* + Qi = Qdi^* \quad \text{(Eq. 17b)}$$

We assume that the upstream flow change effected by the volume change at the upstream port 51 is identical to the upstream flow change effected by the volume change at the downstream port 53: Qui*=Qbui*. Similarly, we assume that the downstream flow change produced by the volume change at the upstream port 51 is identical to the downstream flow change produced by the volume change at the downstream port 53: Qdi*=Qbdi*. These assumptions are closely approximated in cases where the flow resistance between the two sites of the introduced volume change is negligibly small compared to the flow resistances upstream and downstream of the volume change sites. Eqs. 17a and 17b can be rewritten as a single equation with a sensor 50 in only the Qb position:

$$Qbui^* + Qi = Qbdi^* \quad \text{(Eq. 18)}$$

This equation is in a form identical to Eq. 2, but this flow equation is now realized by a two-volume change sites and a single sensor method. Following a derivation approach similar to the one followed for Eq. 2 yields the volume change method equation for this one sensor 50 intermediate two volume change sites 51, 53 configuration:

$$Q = \frac{Qi}{(Cbd - Cbu)} \quad \text{(Eq. 19)}$$

Cbd is the relative change in a flow-corresponding parameter from the upstream volume change introduction. Cbu is the relative change in a flow-corresponding parameter from the downstream volume change introduction.

This equation states that the initial flow in the conduit 10 (vessel) is calculated from the introduced volume change (i.e. ml/min.), and the relative changes (or the values that correspond to these changes) in flow between the locations of the introduced volume change during the first upstream volume change and the second downstream volume change.

The Measurement of Intravascular Blood Flow.

Eight embodiments of a device for the measurement of blood flow in a conduit utilizing the present method and specifically an introduction of known volume change (volume/unit time) into an initial volume flow are disclosed.

In a particular application of the invention, a catheter 20 is disposed in the flow to be measured. That is, the catheter 20 is located inside the flow conduit to provide access for the introduced volume change. The necessary measurements of the resulting flow changes (indicator dilution and/or flow velocity and/or pressure) can be made from sensors carried on the catheter, located in the conduit, located on an exterior to the conduit, on the skin of the patient or even remotely located from the patient.

In addition, the catheter 20 may serve the sole purpose of introducing the volume change, or also accommodate the measurement of the resulting changes in the initial flow, or also be combined with other catheter functions during surgical interventions such as, but not limited to flow restorative procedures performed by the interventional radiologist and cardiologist including balloon angioplasty, thrombectomy, chemical and mechanical clot removal and stenting.

EMBODIMENT 1

Two Sensor Catheter to Measure Velocity with Single Injection

As shown in FIG. 3, in the first embodiment, the catheter 20 with two sensors 30, 40 is employed to measure a velocity of blood (such as in m/sec) using a single volume change introduction through the port 21. The sensors 30, 40 may be any type of sensor as previously disclosed. In a preferred construction, the sensors 30, 40 are connected to the catheter 20 to be located within the conduit 10.

The catheter 20 is inserted into the conduit 10 as shown in FIG. 3. The two sensors 30, 40 measure blood velocity, or a parameter that corresponds to flow velocity at their respective locations in the conduit 10. The first sensor 30 measures a parameter Vu, the second sensor 40 measures a parameter Vd, each corresponding to flow velocity at its local respective site. Because flow velocity corresponds to volume flow, an equation analogous to Eq. 5 is:

$$Q = \frac{Qi}{\left(\frac{\Delta Vd}{Vd} - \frac{\Delta Vu}{Vu}\right)} \quad \text{(Eq. 20)}$$

where $\Delta Vu$ and $\Delta Vd$ are changes corresponding to upstream and downstream blood flow velocities.

The results of Eq. 20 are independent of direct calculation of a value for cross sectional areas of the conduit 10 at the upstream sensor 30 and the downstream sensor 40. An accurate measurement of Q using Eq. 20 relies on the ability to measure baseline values corresponding to flow velocity, Vu and Vd, as well as changes in the baseline $\Delta Vu$ and $\Delta Vd$. The introduced volume change flow rate, Qi may be measured by using a known introduced volume, M, and dividing this known volume by the period of injection, T. Alternatively the introduced change may be implemented by using an infusion/withdrawal pump set to volume change flow rate Qi.

Figure 4A:
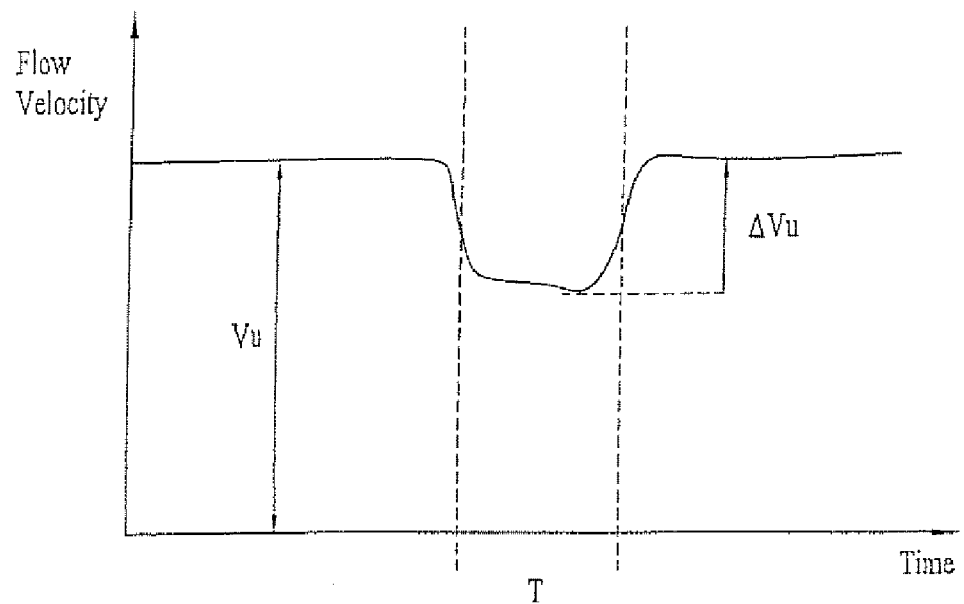
FIG. 4a shows the recorded flow velocity upstream of an introduced volume change.
Figure 4B:
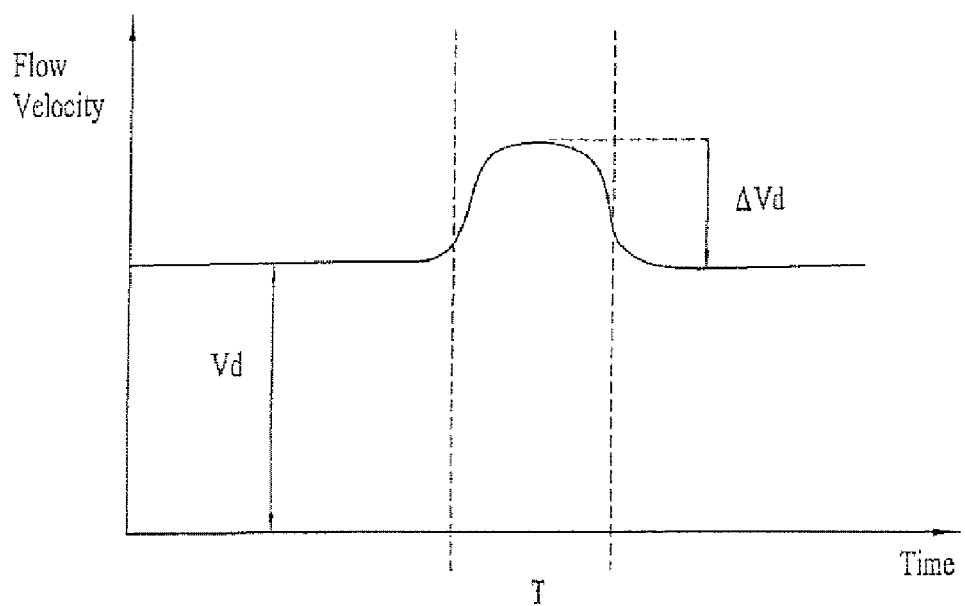
FIG. 4b shows the recorded flow velocity downstream of an introduced volume change.

The introduced volume M may be realized through the injection of a known volume of saline. FIG. 4 illustrates the characteristics of such an injection made between two sensors 30, 40 wherein the sensors provide a signal corresponding to flow velocity. FIG. 4a shows the recorded flow (blood) velocity for the sensor 30 upstream from the site of injection 21, as shown in FIG. 3. FIG. 4b shows the recorded flow (blood) velocity for the sensor 40 located downstream from the site of injection 21. Baseline values Vu and Vd are shown for the upstream and downstream locations, respectively. The decrease in flow (blood) velocity recorded at the upstream sensor ($\Delta$Vu) produced from the injection of duration T is shown in FIG. 4a while the increase in flow (blood) velocity recorded by the downstream sensor ($\Delta$Vd) over the same time period is shown in FIG. 4b. These changes in flow (blood) velocity correspond to $\Delta$Qu and $\Delta$Qd, the changes in the blood flow produced at the upstream and downstream locations, respectively.

EMBODIMENT 2

Velocity Sensors Outside the Vessel with Single Injection

Figure 5:
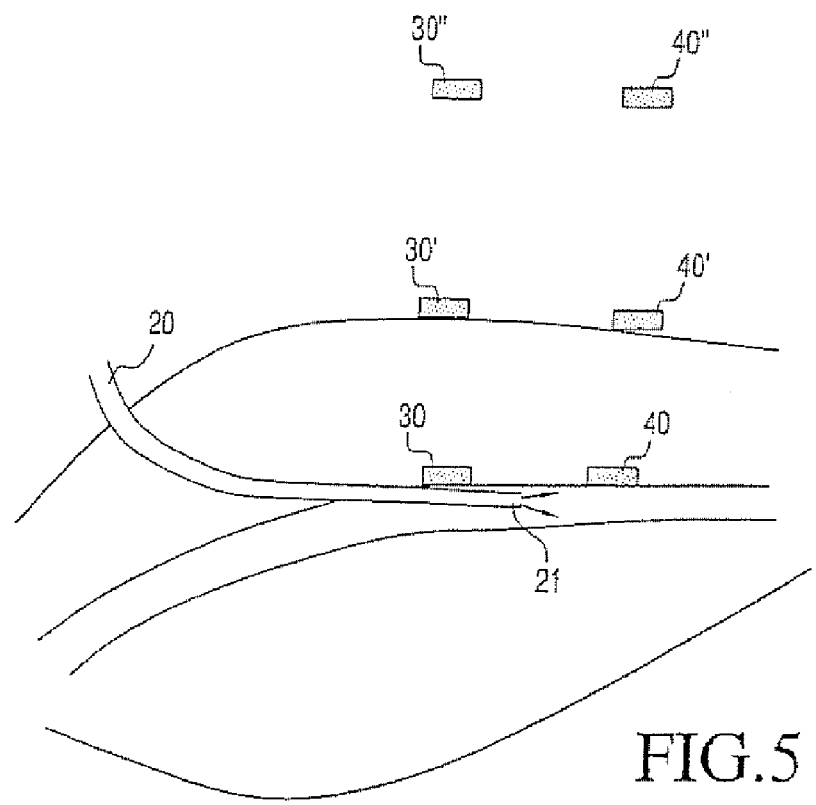
FIG. 5 shows a conduit and site of a volume injection with upstream and downstream sensors located on the conduit, or the skin of a patient and remotely located.

Referring to FIG. 5, in the second embodiment, flow (blood) velocity sensors 30, 40 are located outside the conduit 10 and a single volume change introduction is made through port 21 in the catheter 20 which is located in the conduit. This embodiment is analogous to Embodiment 1 (Eq. 5 and Eq. 20) but sensors 30, 40 are located outside of the conduit 10. Also shown in FIG. 5 are alternative locations for sensors 30', 40' on the skin of the patient, or 30",40" spaced from the patient.

Figure 6:
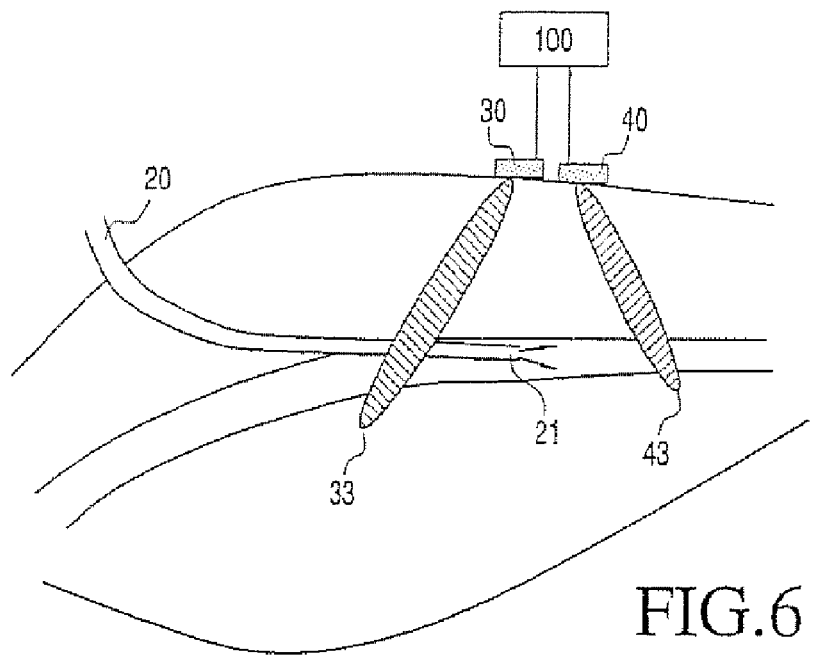
FIG. 6 is a representative view of a conduit and adjacent sensors selected to sense an upstream position and a downstream position respectively.

Referring to FIG. 6, the upstream sensor 30 and the downstream sensor 40 may be adjacent each other and generally aligned along the relevant flow at the injection site 21, wherein each sensor defines a sensing zone such that an upstream sensor 30 sensing zone 33 extends upstream of the injection site and a downstream sensor 40 sensing zone 43 extends downstream of the injection site. In a further configuration shown in FIG. 7, a single sensor 35 may selectively implemented to create an upstream sensing zone 33 and a downstream sensing zone 43.

EMBODIMENT 3

Single Blood Velocity Sensor Catheter with Two Injections

As shown in FIG. 8, the third embodiment employs the catheter 22 having a single flow sensor 50, such as a blood velocity sensor, located intermediate two volume change site ports, an upstream port 51 and a downstream port 53, through which introductions are made into the flow in the conduit 10 through the catheter.

The catheter 22 is inserted into the conduit 10 (FIG. 8). In this embodiment, flow may be measured by making two volume change introductions. One volume change is made upstream through the upstream port 51, the other volume change is made downstream of the single sensor 50 (blood velocity sensor) through the downstream port 53. The equation is analogous to Eq. 19.

$$Q = \frac{Qi}{\left(\frac{\Delta Vd}{V} - \frac{\Delta Vu}{V}\right)} \quad \text{(Eq. 21)}$$

Figure 9:
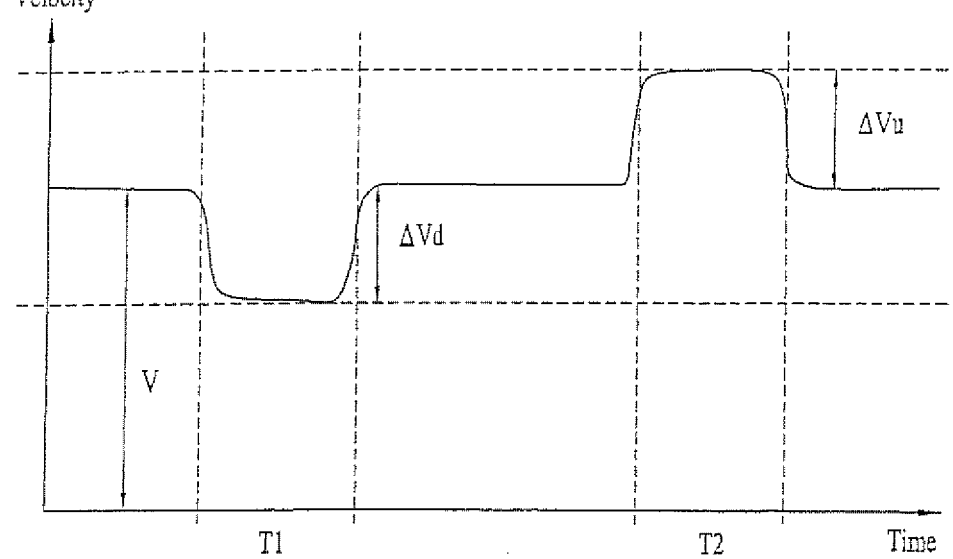
FIG. 9 is a graph showing the relationship of sensed blood velocity to time at a single sensor for a first and a second introduced volume change.

In this equation, V is blood velocity at the location of the single sensor 50; $\Delta$Vd and $\Delta$Vu the changes in blood velocity from a volume change introduction downstream of the sensor and upstream of the sensor respectively. (FIG. 9).

The introduced volume change flow rate, Qi, may be determined by dividing a known injected or withdrawn volume of change, M by the time period of the injection, T.

Intravascular flow can be measured with the single sensor system through the use of two isotonic saline injections. FIG. 9 shows the characteristics of such a method. A baseline blood velocity, V, is measured by the sensor. FIG. 9 shows the first injection. The first injection having been made downstream from the sensor, produces a decrease in V called $\Delta$Vu and occurs in a time period T1. The second injection, made upstream from the sensor, produces an increase in blood velocity at the location of the sensor, $\Delta$Vd, which occurs during time period T2. Volume change injection flow rate, Qi, may be calculated by dividing injected or withdrawn volume M by T1 and T2.

EMBODIMENT 4

Single Blood Velocity Sensor Outside the Conduit with Two Injections

Figure 10:
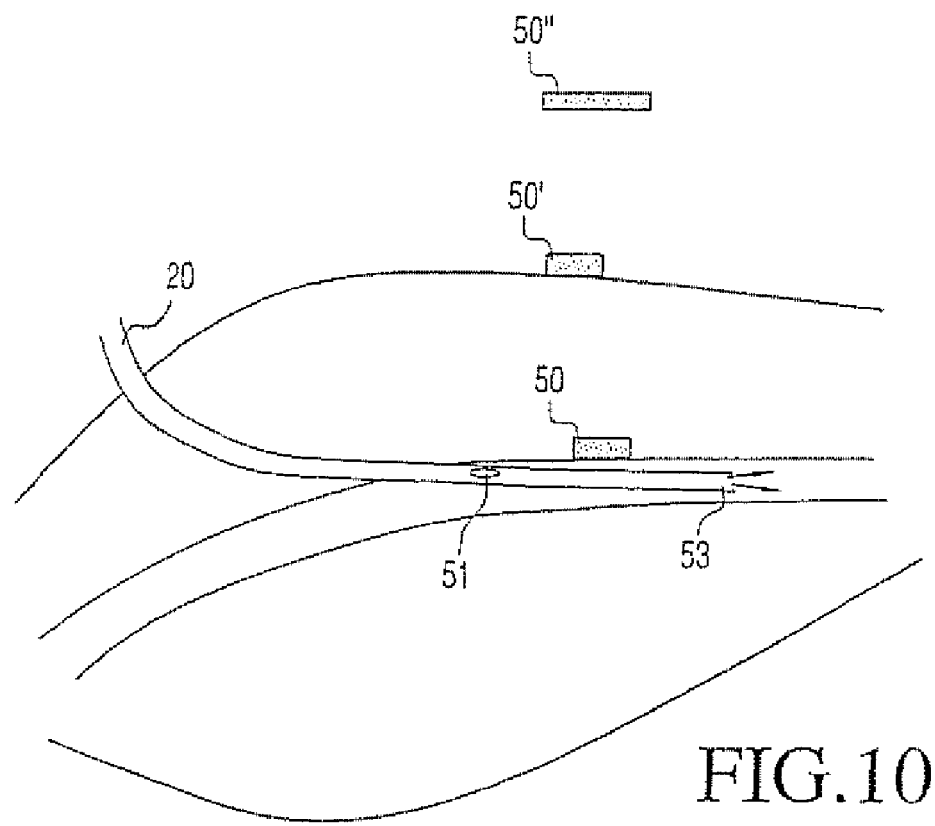
FIG. 10 is a representative view of a conduit showing a sensor outside the conduit in locations at the conduit wall, at the skin of the patient and remotely located.

This approach is analogous to Embodiment 3 and Eq. 21. Referring to FIG. 10, the catheter 20 is disposed into the vessel for providing access for the introduced volume change. The catheter 20 includes an upstream port 51 and a downstream port 53. The sensor 50 such as a blood velocity sensor is located outside the conduit. The location of the sensor 50 is not limited to positioning in between the sites of induced volume change, it is only important that the sensor measures velocity changes between the volume change sites. Also shown in FIG. 10 are alternative sites for sensor 50' on the skin of a patient and 50" spaced from the patient.

Notes on Embodiments 1 Through 4

The blood velocity (corresponding sensors) can derive their measurement from any part of the conduit, even near the walls, assuming the measured parameters correspond to the average flow. Furthermore, only relative changes enter into the calculation, so measured values need only correspond to absolute velocity values. These aspects make the measurement of intravascular flow with the present method relatively simple, with accuracy and reproducibility based mainly on the sensitivity of the device for detecting relative changes corresponding to flow, and accurate determination of the introduced volume change, Qi.

Figure 7:
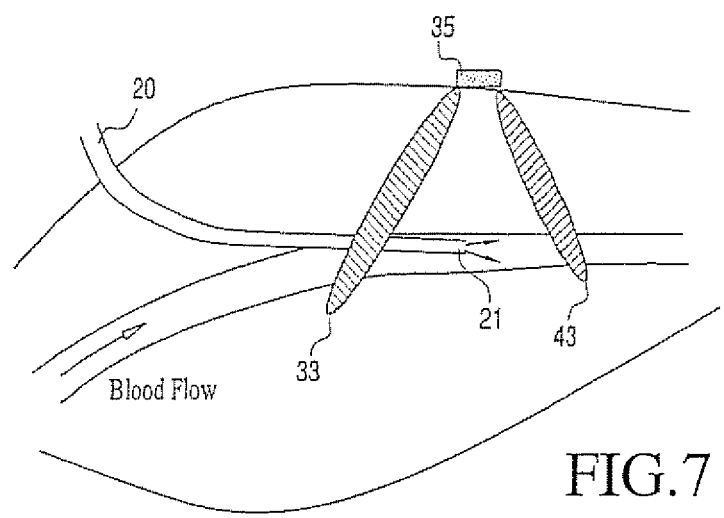
FIG. 7 is a representative view of a conduit and a single sensor sensing an upstream position and a downstream position.

The blood velocity-corresponding sensors may be located at any position where a change may be sensed, such as: inside the conduit 20, on the conduit wall, further removed from the conduit within the patient's body, on the patient's skin, and outside the body. The location of these sensors 50 is not limited to positioning before and after the volume change introduction site. The sensors may be located close to each other but measure blood velocity upstream and downstream the volume change site as shown in FIG. 6. It is contemplated that one sensor 35 as shown in FIG. 7 can be used, wherein the sensor periodically measures blood velocity upstream and downstream of the volume change site. For example, the upstream and downstream measurements can be performed by switching the direction of the generated ultrasound waves. The only requirement on sensor positioning is that one attains the proper upstream/downstream geometric relationship between each sensing site and volume change introduction site as described for Embodiments 1 through 4 and their accompanying figures.

It is also contemplated the sensors and the ports for volume change introduction may be located on different catheters. Volume change introduction may also be made from introducers and other accesses into the conduit such as the sheaths and needles.

In each embodiment, the sensors may be of any type that has the ability to measure relative (blood) flow, relative (blood) velocity or any value corresponding to the flow or the velocity. These sensors may be Doppler (ultrasound or optical), electromagnetic sensors, transit time ultrasound sensors, magnetic resonance sensor, sensors that measure the velocity of blood by recording the injected media movement like X-ray, nuclear magnetic resonance sensors, or any other sensor producing a signal responsive to changes in flow.

EMBODIMENT 5

Figure 11:
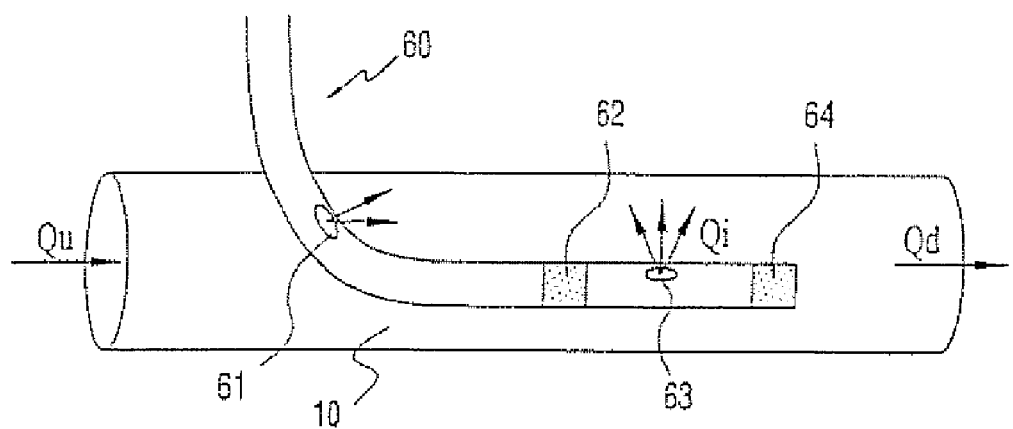
FIG. 11 is a representative view of a conduit showing an indicator dilution catheter with two separate dilution sensors for a constant infusion in combination with a single volume change.

Indicator Dilution Catheter with Two Separate Dilution Sensors Using Constant Infusion Combined with Single Volume Change Referring to FIG. 11, this configuration employs an indicator dilution catheter 60 using constant infusion in conjunction with a single volume change introduction. In one construction of this configuration, the catheter 60 includes a constant infusion port 61 and a volume change port 63 an upstream sensor 62 intermediate the constant infusion port and the volume change port, and a downstream sensor 64 downstream of the volume change port. This embodiment describes intravascular flow measurement using a catheter 60 with a dilution sensor 62 which is inserted into the conduit 10. The constant infusion should have a duration sufficient to overlap the volume change period. To measure the relative changes of blood flow pursuant to Equation 5, a change in indicator concentration is monitored.

The upstream sensor 62 (a dilution sensor) is located upstream of the volume change port 63 and the downstream sensor 64 is disposed downstream of the volume change port 63. For purposes of description, the upstream sensor measurements are designated with a "u", and the downstream sensor measurements are designated with a "d" suffix.

The constant infusion serves to introduce an indicator upstream from both the sensors 62, 64. This indicator may be introduced anywhere within the cardiovascular system, such as in a vein from where it passes through the heart into the artery where the volume change catheter 60 is positioned. The following mathematical relationship exists for the initial blood flow Q in the conduit 10 to be measured:

$$Q = Qu = Qd = \frac{qku}{hu} = \frac{qkd}{hd} \qquad \text{(Eq. 22)}$$

In Equation 22, q is the rate of indicator infusion into conduit, ku and kd are calibration coefficients for the upstream sensor 62 and the downstream sensor 64, respectively, hu and hd are the concentration of the indicator measured at the upstream sensor 62 and the downstream sensor 64, respectively, as shown in FIG. 12.

An introduction of blood volume change between the sensors 62, 64 produces a change in indicator concentration measured at the upstream sensor 62 and a change in the conduit volume flow. The new flow equation is described mathematically in Equation 23a:

$$Qui = \frac{qku}{hui} \qquad \text{(Eq. 23a)}$$

Figure 12A:
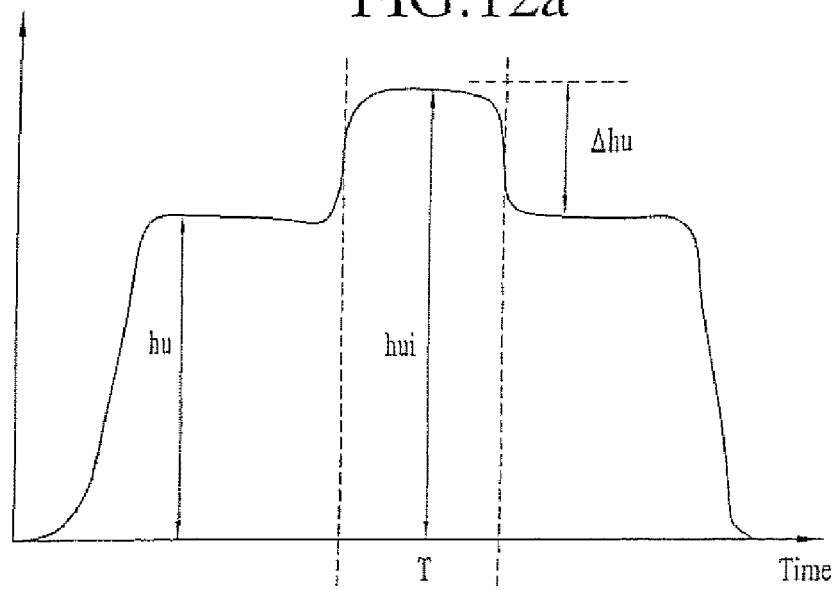
FIG. 12a is a graph showing the relationship of sensed indicator concentration to time at an upstream sensor after the introduced volume change.

In Equation 23a, hui is the new level of the concentration recorded by the upstream sensor 62 (see FIG. 12a).

The same injection also produces a new level of flow and indicator concentration at the second (downstream) sensor 64:

$$Qdi = \frac{qkd}{hdi} \qquad \text{(Eq. 23b)}$$

Figure 12B:
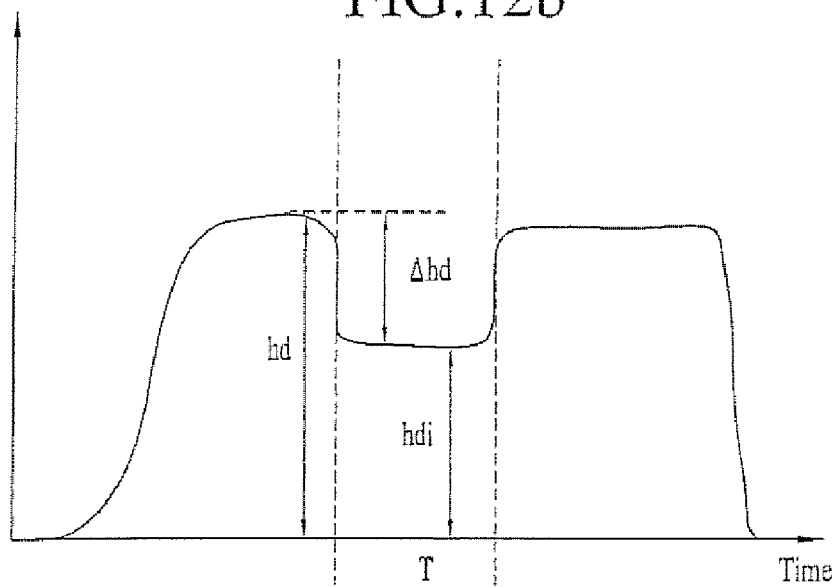
FIG. 12b is a graph showing the relationship of sensed indicator concentration to time at a downstream sensor after the introduced volume change.

In Equation 23b, hdi is the new level of the concentration recorded by the downstream sensor 64 (FIG. 12b).

With a known introduced volume change flow rate, Qi, we substitute Equations 23a and 23b into the conservation of mass Eq. 2:

$$Qi = q\left(\frac{kd}{hdi} - \frac{ku}{hui}\right) \qquad \text{(Eq. 24)}$$

Substituting Equation 22 into Equation 24 yields Equation 25:

$$Q = \frac{Qi}{\left(\frac{hd}{hid} - \frac{hu}{hui}\right)} \qquad \text{(Eq. 25)}$$

Using indicator concentration change definitions: $\Delta hu=hui-hu$; $\Delta hd=hdi-hd$, this equation can be re-written in terms of relative indicator concentration change:

$$Q = \frac{Qi}{\left(\frac{\Delta hu}{hui} - \frac{\Delta hd}{hdi}\right)} \qquad \text{(Eq. 26)}$$

One finds from FIG. 12 that $\Delta hd$ is negative; the denominator of Eq. 26 is the sum of two positive numbers. Introduced volume change flow rate (Qi) can be calculated as a ratio of known volume change injection (M) divided by the time length of injection, T. The time period of the injection may be recorded simply from the profile change of the dilution curves (see FIG. 12). As is the case for all volume change embodiments, one does not need to know the value of calibration coefficients ku and ku of the indicator concentration sensors. All concentration levels in Eq. 26 are expressed as ratios, meaning that only relative-sensing indicator devices are needed to implement the volume change method.

EMBODIMENT 6

Figure 13:
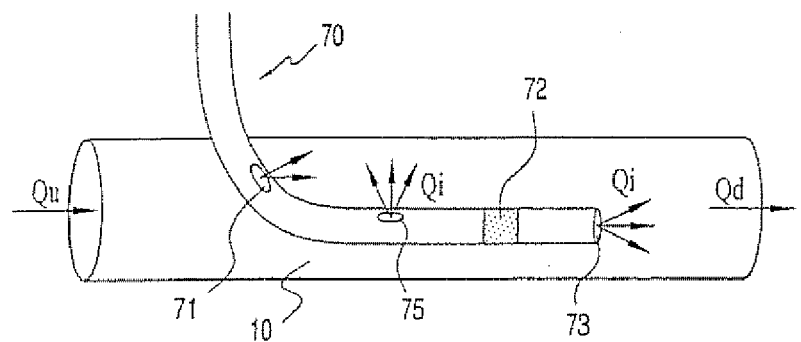
FIG. 13 is a representative view of a conduit showing a catheter having an indicator dilution sensor for use with a constant infusion combined with two separate injections.

Indicator Dilution Catheter Using Constant Infusion Combined with Two Separate Injections (FIG. 13)

Referring to FIG. 13, this embodiment describes intravascular flow measurement using a catheter 70 having a dilution sensor 72 which is inserted into the conduit 10. The catheter 70 includes an indicator infusion port 71, an upstream volume change introduction port 75 and a downstream volume change introduction port 73, wherein the sensor 72 is intermediate the upstream volume change introduction port and the downstream volume change introduction port.

The first part of this method involves the creation of a continuously introduced indicator upstream from the dilution sensor 72. This may be accomplished through the upstream port 71. Initial flow in the conduit 10 (vessel) Q to be measured is then described mathematically as follows:

$$Q = q\frac{k}{h} \quad \text{(Eq. 27)}$$

In this equation q is the rate of indicator infusion, k is the calibration coefficient related to the catheter sensitivity, and h is the concentration level of the indicator during the infusion.

Figure 14:
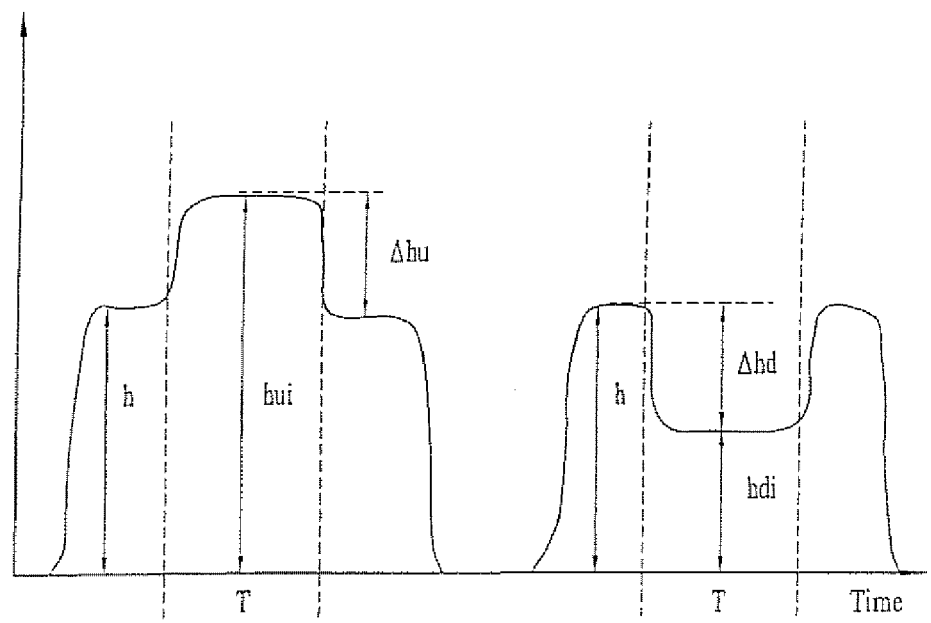
FIG. 14 is a graph showing the relationship of sensed indicator concentration to time at a dilution sensor for a first and a second introduced volume change.

As a next step, a first Qi* volume change is introduced in the conduit 10 (vessel) via port 73 in the catheter 70. The dilution sensor 72 located upstream from the volume change site senses a new indicator concentration level hui (FIG. 14). The new upstream flow Qui is described mathematically in Equation 28.

$$Qui = q\frac{k}{hui} \quad \text{(Eq. 28)}$$

A second volume change, Qi* is introduced via port 75. The dilution sensor 72 located downstream from the volume change site at 75. Equation 29 describes this mathematical relationship:

$$Qdi = q\frac{k}{hdi} \quad \text{(Eq. 29)}$$

In Equation 29, Qdi is flow at the dilution sensor location during the upstream volume change, hui is the new level of the concentration recorded by the sensor 72.

For simplicity, it is assumed that volume change injection flow, Qi*, was the same for both upstream and downstream volume changes. This assumption allows us to follow the derivation steps of Eqs. 24-26 to arrive at the following mathematical relationship:

$$Q = \frac{Qi}{\left(\frac{\Delta hu}{hui} - \frac{\Delta hd}{hdi}\right)} \quad \text{(Eq. 30)}$$

Thus, embodiment 5 and 6 are mathematically identical, and all definitions and comments made for Eq. 26 apply to Eq. 30 as well.

Notes on Embodiments 5 and 6

The indicator introduction may be performed from the same catheter where dilution sensor(s) are located or through another catheter or through the introducer, or through a needle. The indicator introduction further includes but is not limited to adding substances to blood, withdrawing substances from blood or changing blood parameters (like heating or cooling) without adding or withdrawing substances from blood.

The indicator introduction may be performed anywhere within the cardiovascular system, for example, into a vein from where it passes through the heart into the artery where the volume change catheter is positioned.

Usually the indicator infusion (or withdrawal) rate is much smaller than the initial blood flow rate and its influence on the initial blood flow in the conduit may me ignored. In the case of heating or cooling of blood the indicator introduction causes no change in flow rate at all. In certain instances one may purposely choose an indicator introduction which doubles as a volume change introduction, and so arrange a measurement sequence of steps or catheter configuration which is advantageous for certain interventional procedures. For instance, the second volume change Qi* in the upstream site described in Eq. 29 may be implemented with an injection solution which incorporates the indicator agent as well, eliminating the need for the upstream continuous indicator infusion during this step of the procedural sequence. This approach would eliminate the need for a separate upstream port for a volume change introduction.

In embodiments 5 and 6 the value of h is a concentration of indicator in blood. The embodiments may use common indicators but is not limited to these: blood hematocrit, blood protein, sodium chloride, dyes, blood urea nitrogen, glucose, lithium chloride and radioactive isotopes and microspheres. The blood concentration factors h appears in Eqs. 26 and 30 only in the form of dimension-less ratios. This means that in these embodiments no need exists for methods and devices which register indicator concentration in absolute, calibrated units. Instead one may employ any method and device that produces relative, proportional or corresponding indications of a selected blood concentration. One may thus select sensors which register values or its changes of any chemical or physical parameters of blood that correspond to concentration. These embodiments may thus use, but are not limited to the following blood properties such as: blood electrical impedance, optical blood properties, blood temperature, blood density, blood pH, as well as blood ultrasound velocity. The sensors in each embodiment include any type of sensors that record a corresponding measurement to such selected blood properties.

The indicator sensors may be located outside the conduit 10 (vessel), but preferably record the dilution curves in the vessel locations upstream and downstream from the injection flow (embodiment 5) and between the injection flow locations for embodiment 6. These sensors may be, but are not limited to, electrical impedance sensors, ultrasound sensors and optical sensors.

It is further clear from Eq. 26 and 30 that the volume change approach does not require that the calibration coefficient k (see Eq. 22 and 27) be known. The results of the volume change measurement can be used instead to calibrate dilution sensors by calculating the value of k. Once the value of k is calculated, the same sensor can thereafter be employed as a conventional indicator dilution sensor, with no need to perform separate volume change introductions.

EMBODIMENT 7

Two Sensor Catheter to Measure Pressure with Single Injection

Figure 15:
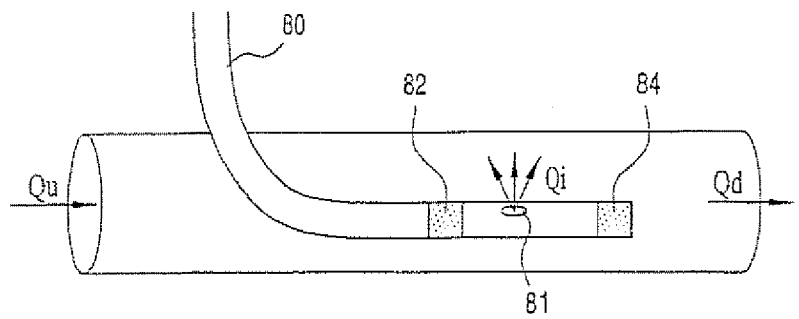
FIG. 15 is a representative view of a catheter in a conduit, the catheter having two pressure sensors and one intermediate volume change site.

In a seventh embodiment shown in FIG. 15, a catheter 80 with two sensors 82, 84 and an intermediate volume change injection port 81 is employed which measure blood pressure before and during a single volume change introduction. The sensors 82, 84 may be any type of pressure sensors. Further, the pressure sensors may be located inside or outside the conduit 10.

In a preferred construction, the sensors 82, 84 are connected to the catheter 80 to be inserted into the conduit 10 as shown in FIG. 15. The two sensors 82, 84 measure blood pressure or a parameter that corresponds to blood pressure at their respective locations in the conduit 10. The first sensor 82 measures an upstream value Pu and the second sensor 84 measures a downstream value Pd.

Figure 16:
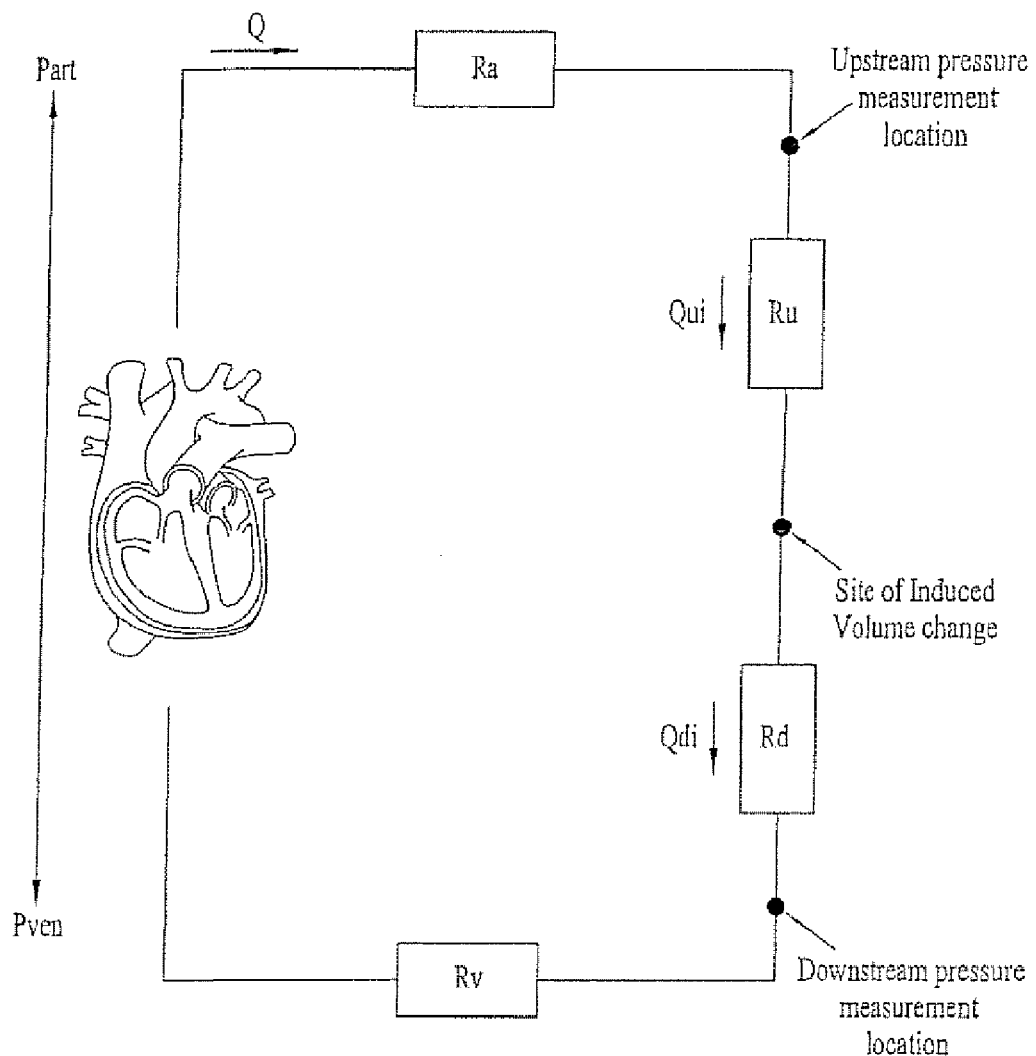
FIG. 16 is a hydrodynamic schematic of a cardiovascular system during blood flow measurement by induced volume change using a single volume change and two pressure sensors.

Referring to FIG. 16, the volume change equation for determining flow in this embodiment can be derived from a hydrodynamic model of blood circulation in the vascular system. In FIG. 16, Ra and Rv represent the hydrodynamic resistances of the arterial and venous sides of the cardiovascular circuit leading to the upstream and downstream sensor sites, respectively. Ru and Rd are the hydrodynamic resistances of the flow conduit between the place of the volume change introduction and the upstream and the downstream sensor locations respectively.

The flow-pressure equations before the volume change introduction in Embodiment 7 are as follows:

$$Part - Pu = QRa \quad \text{(Eq. 31)}$$

$$Pd - Pven = QRv \quad \text{(Eq. 32)}$$

During the volume change, conservation of mass at the volume change point is described by Eq. 2: Qui+Qi=Qdi. Therefore:

$$Part - Pui = QuiRa \quad \text{(Eq. 33)}$$

$$Pdi - Pven = QdiRv \quad \text{(Eq. 34)}$$

where Pui and Pdi are the new pressure levels in upstream and downstream location respectively; Qui and Qdi are the new flows through the branches upstream and downstream from the volume change introduction place. Substituting Eqs. 33 and 34 into Eq. 2 yields:

$$Qi = (Pdi - Pven)/Rv - (Part - Pui)/Ra \quad \text{(Eq. 35)}$$

In this equation, the variables Ra and Rv can be eliminated using Eqs. 31 and 32:

$$Qi = Q\{(Pdi - Pven)/(Pd - Pven) - (Part - Pui)/(Part - Pu)\} \quad \text{(Eq. 36)}$$

The pressures at the upstream and downstream sensing location are expressed in terms of their change:

$$\Delta PU = Pui - Pu \quad \text{(Eq. 37)}$$

$$\Delta Pd = Pdi - Pd \quad \text{(Eq. 38)}$$

Rearranging the terms then yields one of the expressions for flow Q as determined from the volume change Qi and pressure changes at the upstream and downstream sensing points:

0

This is one of a number of ways to express the flow equation of the volume change method when using pressure sensors. Pressure is a quantity which is always expressed relative to another site, as only pressure differences may produce flow. The Pd and Pu pressures may thus be referenced to a number of points within the cardiovascular system, each producing a different form for Eq. 39. As an example, Pu and Pd may be referenced to the point of the volume change introduction, Pi. In this instance the flow Q would be determined only from pressure differences registered on points along for instance a catheter containing the volume change introduction port and three pressure sensors.

Figure 17A:
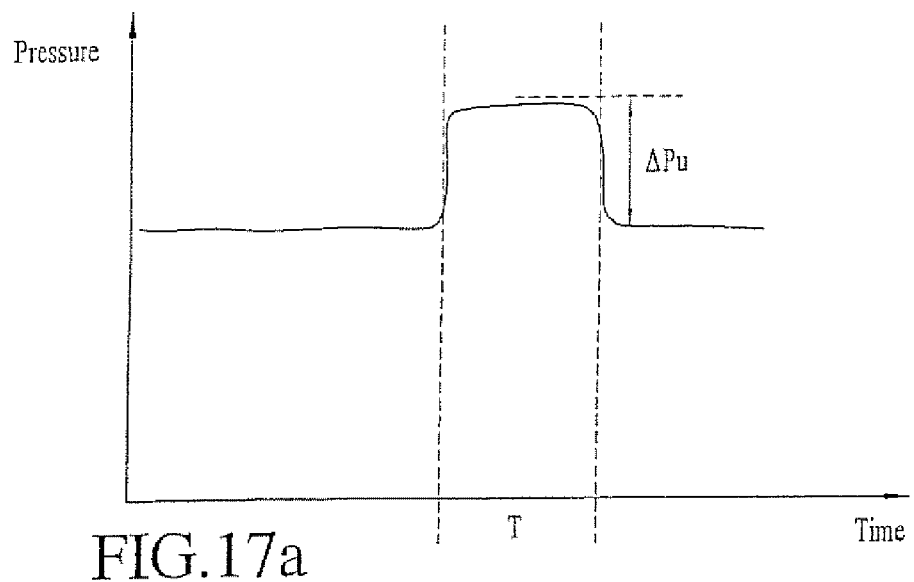
FIG. 17a shows the recorded pressures upstream of an induced volume change.
Figure 17B:
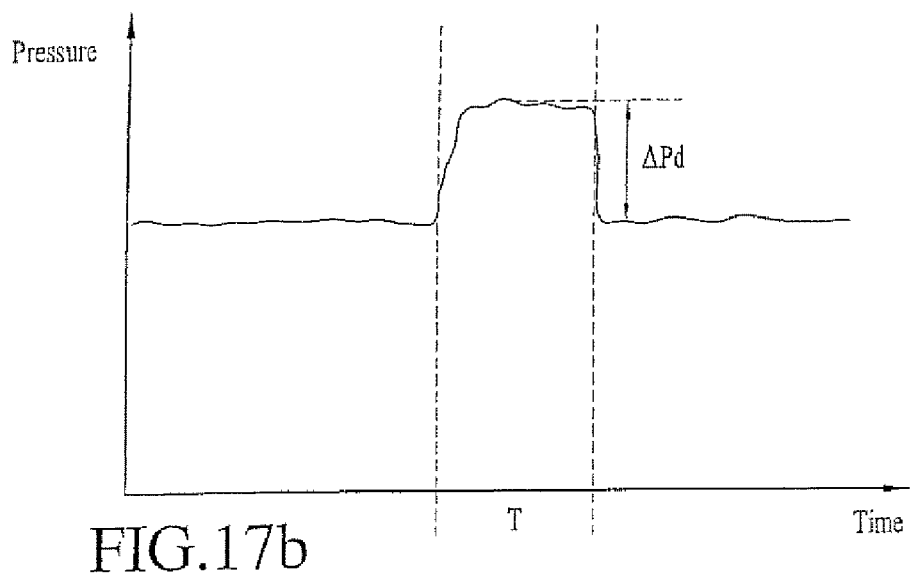
FIG. 17b shows the recorded pressures downstream of an induced volume change.

This type of intravascular flow measurement may be through injection of a known volume (M) of isotonic saline. FIG. 17a shows the recorded blood pressure for a sensor upstream from the site of injection. FIG. 17b shows the recorded blood pressure for a sensor located downstream from the site of injection. Baseline pressure values Pu and Pd are shown for the upstream and downstream locations, respectively.

EMBODIMENT 8

Single Blood Pressure Sensor Catheter with Two Injections

Figure 18:
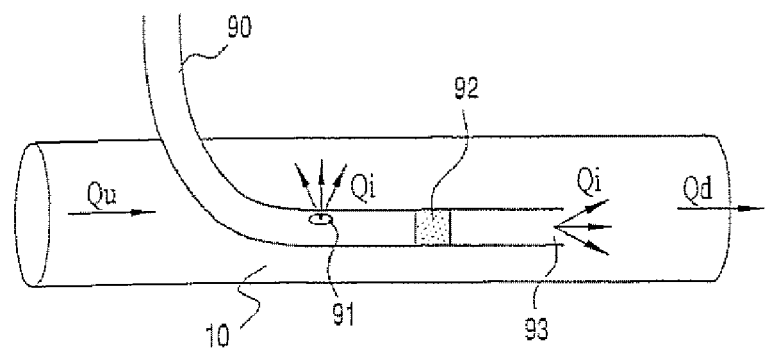
FIG. 18 is a representative view of a catheter in a conduit, the catheter having a single pressure sensor intermediate a pair of volume change sites.
Figure 19:
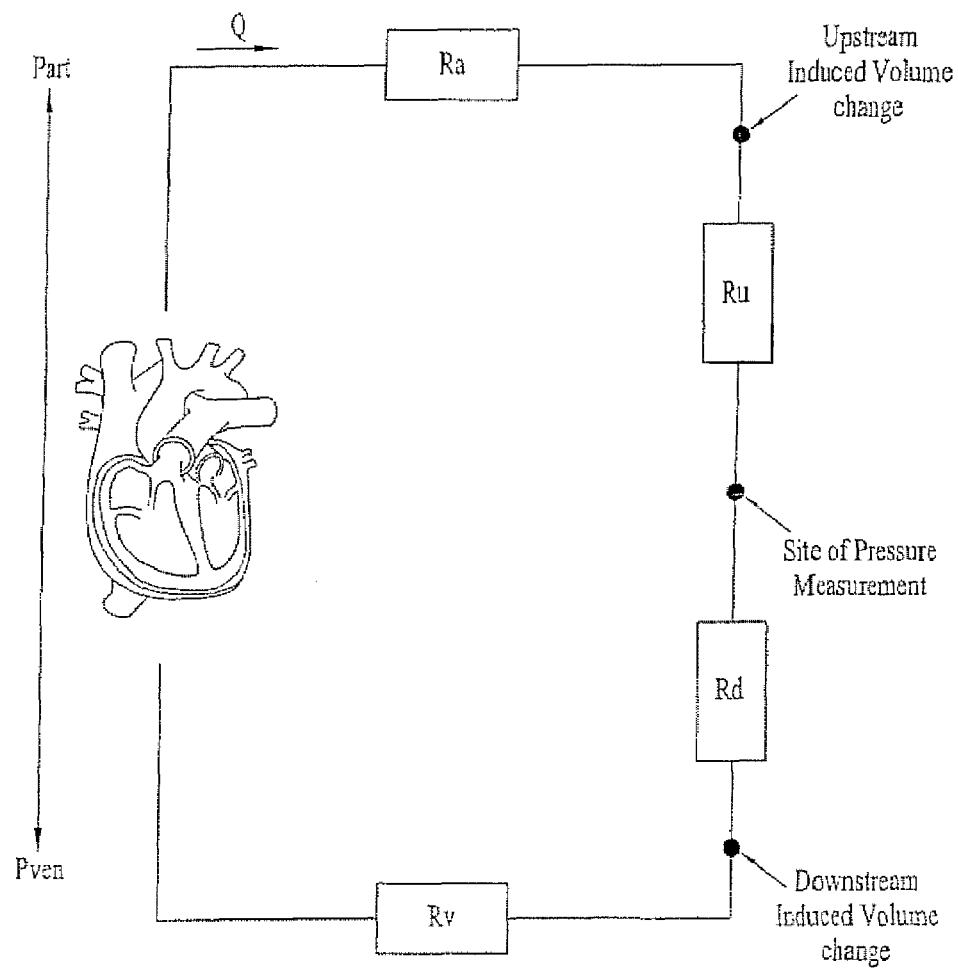
FIG. 19 represents the hydrodynamic schematic diagram of the cardiovascular system during blood flow measurement by introduced volume change using two volume changes and a single pressure sensor.

As shown in FIG. 18, the eighth embodiment employs a catheter 90 having a single flow (blood) pressure sensor 92, an upstream volume change introduction port 91 and a downstream volume change introduction port 93, wherein two volume change introductions can be made into the flow in the conduit 10 through the catheter 90.

The catheter 90 is inserted into the conduit 10 (FIG. 18). In this embodiment, one volume introduction is made upstream of the sensor and one is made downstream of the single blood pressure sensor. The volume change equation for this embodiment is derived in steps analogous to Eq. 39:

$$Q = \frac{Qi}{\left(\frac{\Delta Pd^*}{Pd - Pven} - \frac{\Delta Pu^*}{Pu - Part}\right)} \quad \text{(Eq. 40)}$$

where Pu and Pd are blood pressures measured at the sensor site(s) before each volume change introduction, $\Delta Pu^*$ and $\Delta Pd^*$ are the changes of the pressure due to volume change introduction upstream and downstream of the sensor 92 respectively.

Figure 20:
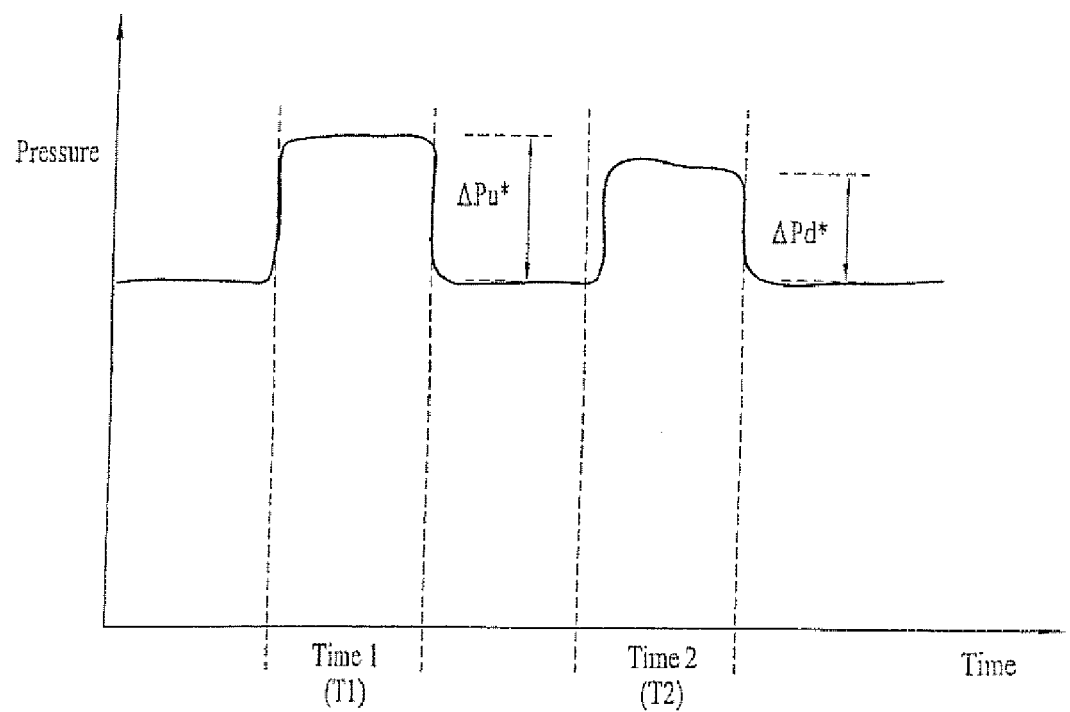
FIG. 20 is graph showing the relationship of sensed pressure for a first and a second induced volume change.

Intravascular flow can be measured with the single sensor system through the use of two isotonic saline injections. FIG. 20 shows the characteristics of such a method. FIG. 20 shows the first injection, made upstream from the sensor. This injection produces a pressure increase in $\Delta Pu^*$ and occurs in a time period T1. The second injection, made downstream from the sensor, also produces also increase in blood pressure $\Delta Pd^*$ at the location of the sensor, which occurs during time period T2. Volume change injection flow, Qi, may be calculated by dividing injection or withdraw volume (M) by T1 and T2.

Notes on Embodiments 7 and 8

Pressure measurements can be performed using any customary pressure sensing system located inside or outside the conduit. In a dual sensor system ($7^{th}$ embodiment) one sensor may even be inside the conduit 10 while the other is outside the conduit. Sensors as customarily used are liquid-filled catheters with a mechanical or electronic sensing device positioned at the end of the catheter outside the patient, electronic sensors positioned on the catheter inside the patient, but any other sensor system would suffice.

The volume change method may be implemented with further simplifications in catheter configuration and sensor/injection port implementation. As an example, embodiment 8 can be implemented using a double lumen catheter with each lumen channel alternately functioning as a volume change port and liquid-filled pressure sensing channel. During a volume change through the upstream port 91, pressures are sensed from the downstream port 93 and vice versa. It is also understood the sensor 92 may be omitted and the pressure monitored through the port which does not provide the respective volume change. As another example, one may use an extracorporeal pressure sensor positioned on the skin above an artery, and position a volume change introduction catheter inside that artery to sequentially produce an upstream and a downstream volume change introduction. Such sequential volume change introductions may consist, first, of the withdrawal of a volume of blood, then of the re-injection of the same volume of blood.

Embodiments Employing Combinations of Blood Velocity Measurement, Dilution Measurement, and Blood pressure Measurement It is clear from Eq. 4, 20, 26, and 39 that the upstream flow changes upon a volume change introduction are recorded independently of the downstream flow changes upon a volume change introduction. This offers the design freedom to mix and match all the sensing modalities disclosed in the previous embodiments (blood flow or velocity sensing, indicator concentration sensing, blood pressure sensing), with one modality selected for the upstream, another modality for the downstream sensor. For example, relative flow change in the upstream location may be measured by a Doppler blood velocity sensor and simultaneously downstream changes may be recorded by a pressure sensor. Alternately, an upstream dilution sensor may be combined with a downstream pressure sensor, an intravascular pressure sensor may be combined with an extracorporeal flow velocity sensor, as examples. In such a fashion the designer of volume change instrumentation systems is given optimum design freedom to customize the measurement apparatus to suit a targeted the surgical procedure.

Notes on All Discussed Embodiments

The volume change method may be used anywhere within the cardiovascular system: in arteries, veins, in the heart, in arterio-venous shunts and other conduits within the body where flow can be altered via a volume change introduction.

Besides providing intravascular flow measurements, an added benefit of the volume change method is the analysis of the relationship between the upstream and the downstream flow ratios ($\Delta Vu/Vu$ vs. $\Delta Vd/Vd$ in Equation 20 and the analogous expressions in Eqs. 21, 26, 30, 39 and 40). Comparison of these ratios provides the user an indication of where the main resistance to the blood flow is located. In the case of vascular flow restorative procedures such as angioplasty, the main resistance to flow identifies the most hemodynamically significant stenosis, allowing the operator to correct the most serious flow impediment when multiple stenoses are present. For example, when $\Delta Vu/Vu$ is high when compared to $\Delta Vd/Vd$, it means that there is a large resistance downstream from the site of injection. When $\Delta Vd/Vd$ and $\Delta Vd/V$ are high, there is a significant limitation to flow located upstream from the injection site. The ability to analyze this data allows the operator greater efficiency in treating a stenosed vessel, reducing the need to correct a stenosis and then check flow in a trial and error attempt to identify the major limitation to flow.

For embodiments employing the sequential volume change in an upstream and a downstream location, one may employ a single lumen catheter with upstream and downstream ports having one-way valves incorporated. The one-way valves would be constructed such that a flow injection automatically opens one port, and a flow withdrawal automatically the other port. Alternately such a single lumen catheter may employ alternate means to switch the volume change delivery between the upstream and the downstream port. Alternately one may use a single lumen, single outlet catheter, and reposition the catheter outlet in relation to the sensor (or vice versa) to achieve the desired upstream positioning during one, and downstream positioning during the other volume change.

As it is clear from the flow equations 4, 20, 21, 26, 30, 39 and 40, blood velocity, blood properties and blood pressure values are present only in the form of non-dimensional ratios. This means that all these embodiments may instead employ uncalibrated sensors or sensors that only provide values corresponding to the parameter referenced in the flow equations. Such corresponding sensors measurements may produce any measurement dimension such as "kilohertz" for an ultrasound Doppler sensor, or "bits" for an analog-to-digital converter output: these dimensions are eliminated in the flow equation in the non-dimensional sensor ratio expression.

The present invention contemplates a controller 100 for determining or calculating the initial flow rate in the conduit 10 in response to the corresponding signals from the respective sensor(s) and the introduced volume change(s). The controller 100 may be any of a variety of devices including a computer employing software for performing the calculations, or a dedicated analog circuit device, or a calculation routine into which measured parameters are manually entered. The controller 100 may be connected to the sensor(s) and a flow rate monitor such as a pump for introducing the volume change. It is understood the controller 100 could determine the volume change from an input of the volume of the change and the time over which the change was made.

While a preferred embodiment of the invention has been shown and described with particularity, it will be appreciated that various changes and modifications may suggest themselves to one having ordinary skill in the art upon being apprised of the present invention. It is intended to encompass all such changes and modifications as fall within the scope and spirit of the appended claims.

The invention claimed is:

1. A method for determining an initial flow rate in a conduit, comprising:
   (a) introducing a volume change to the initial flow rate at a location, the introduced volume change predominately flowing retrograde to an initial flow in the conduit, producing a resulting change upstream of the location; and
   (b) determining the initial flow rate corresponding to the introduced volume change and the resulting change.

2. The method of claim 1, further comprising measuring a resulting change upstream from the location.

3. A method of determining an initial flow rate in a conduit, comprising:
   (a) determining the initial flow rate corresponding to the following equation and analogous relationships, $$Q = \frac{Qi}{Cd - Cu},$$

where Qi is the volume change flow rate, Cd is the relative change in a flow corresponding parameter downstream from a location of flow change, Cu is the relative change in a flow corresponding parameter upstream from the location of the flow change, and a Q is the initial flow rate.

4. A method for determining an initial flow rate in a conduit, comprising:
(a) determining the initial blood flow rate corresponding to the following equation and analogous relationships, $$Qh = \frac{Qi}{Cd},$$

where Qh=initial flow rate, Qi=a flow rate of the volume change $$Cd = \frac{\Delta Qd}{Qd},$$

ΔQd=change in a downstream flow rates and Qd is the downstream flow rate.

5. A method for determining an initial flow rate in a conduit, comprising:
(a) determining the initial flow rate corresponding to the following equation and analogous relationships, $$Qc = \frac{Qi}{Cu},$$

where Qc=the initial flow rate, Qi=the flow rate of the volume change and Cu=the relative change in a flow corresponding parameter upstream of a location of the volume change.

6. A method for determining an initial flow rate and a conduit, comprising:
(a) determining the initial flow rate corresponding to the following equation and analogous relationships $$Qv = \frac{Qi}{Cd+1},$$

where Qi=the flow rate of the volume change, Cd=the relative change in a flow corresponding parameter downstream of a flow change, and Qv=is the initial flow rate.

7. An apparatus for determining an initial flow rate in a conduit, comprising:
(a) a catheter having an upstream port and a downstream port;
(b) means for introducing a volume change through the upstream port and the downstream port;
(c) a velocity sensor located external to the conduit; and
(d) a controller connected to the means for introducing volume change and the velocity sensor, the controller configured to determine the initial flow rate.

8. A method for determining an initial flow rate in a conduit, the method comprising:
(a) introducing a constant rate infusion into the initial flow;
(b) introducing a first volume change to the initial flow upstream of a sensor;
(c) introducing a second volume change to the initial flow downstream of the sensor; and
(d) determining the initial flow rate corresponding to the first volume change and the second volume change.

9. An apparatus for determining an initial flow rate in a conduit, comprising:
(a) a catheter having an infusion port, a volume change port, an upstream sensor intermediate the infusion port and the volume change port, and a downstream sensor located downstream of the volume change port;
(b) means for introducing a constant infusion through the infusion port;
(c) means for introducing a volume change through the volume change port; and
(d) a controller connected to the upstream sensor and the downstream sensor for determining the initial flow rate corresponding to the introduced volume change.

10. An apparatus for determining an initial flow rate in a conduit, comprising:
(a) a catheter having a pair of volume change ports, a sensor intermediate the volume change ports and an infusion port upstream of the pair of volume change ports;
(b) means for introducing a constant infusion through the infusion port;
(c) means for introducing a first volume change through one of the volume change ports and a second volume change through a remaining one of the volume change ports; and
(d) a controller connected to the sensor for determining the initial flow rate corresponding to the introduced volume changes.

* * * * *